United States Patent
Stoltz et al.

(10) Patent No.: US 7,367,969 B2
(45) Date of Patent: May 6, 2008

(54) ABLATIVE MATERIAL REMOVAL WITH A PRESET REMOVAL RATE OR VOLUME OR DEPTH

(75) Inventors: Richard Stoltz, Plano, TX (US); Peter J. Delfyett, Oviedo, FL (US)

(73) Assignee: Raydiance, Inc., Orlando, FL (US)

( * ) Notice: Subject to any disclaimer, the term of this patent is extended or adjusted under 35 U.S.C. 154(b) by 628 days.

(21) Appl. No.: 10/916,365

(22) Filed: Aug. 11, 2004

(65) Prior Publication Data

US 2006/0064079 A1    Mar. 23, 2006

Related U.S. Application Data

(60) Provisional application No. 60/503,578, filed on Sep. 17, 2003, provisional application No. 60/494,273, filed on Aug. 11, 2003.

(51) Int. Cl.
*A61B 18/18* (2006.01)
*A61B 18/20* (2006.01)

(52) U.S. Cl. .............. 606/9; 606/10; 606/12; 607/88; 607/89; 128/898

(58) Field of Classification Search .......... 606/3–12; 607/88, 89; 128/898; 216/65, 66, 87; 359/333, 359/342–349

See application file for complete search history.

(56) References Cited

U.S. PATENT DOCUMENTS

| | | |
|---|---|---|
| 3,631,362 A | 12/1971 | Almasi et al. |
| 3,808,549 A | 4/1974 | Maurer |
| 3,963,953 A | 6/1976 | Thornton, Jr. |
| 4,718,418 A | 1/1988 | L'Esperance, Jr. |
| 4,750,809 A | 6/1988 | Kafka et al. |
| 4,815,079 A | 3/1989 | Snitzer et al. |
| 4,824,598 A | 4/1989 | Stokowski |
| 4,829,529 A | 5/1989 | Kafka |
| 4,902,127 A | 2/1990 | Byer et al. |
| 4,913,520 A | 4/1990 | Kafka |
| 4,972,423 A | 11/1990 | Alfano et al. |
| 5,098,426 A | 3/1992 | Sklar et al. |
| 5,162,643 A | 11/1992 | Currie |
| 5,166,818 A | 11/1992 | Chase et al. |
| 5,187,759 A | 2/1993 | DiGiovanni et al. |
| 5,237,576 A | 8/1993 | DiGiovanni et al. |
| 5,265,107 A | 11/1993 | Delfyett, Jr. |
| 5,291,501 A | 3/1994 | Hanna |
| 5,302,835 A | 4/1994 | Bendett et al. |
| 5,313,262 A | 5/1994 | Leonard |
| 5,329,398 A | 7/1994 | Lai et al. |
| 5,400,350 A * | 3/1995 | Galvanauskas ............ 372/20 |
| 5,414,725 A | 5/1995 | Fermann et al. |
| 5,418,809 A | 5/1995 | August, Jr. et al. |
| 5,430,572 A | 7/1995 | DiGiovanni et al. |
| 5,440,573 A | 8/1995 | Fermann |
| 5,450,427 A | 9/1995 | Fermann et al. |
| 5,479,422 A | 12/1995 | Fermann et al. |
| 5,489,984 A | 2/1996 | Hariharan et al. |
| 5,499,134 A | 3/1996 | Galvanauskas et al. |
| 5,517,043 A | 5/1996 | Ma et al. |
| 5,572,335 A | 11/1996 | Stevens |
| 5,572,358 A | 11/1996 | Gabl et al. |
| 5,585,652 A | 12/1996 | Kamasz et al. |
| 5,585,913 A | 12/1996 | Hariharan et al. |
| 5,592,327 A | 1/1997 | Gabl et al. |
| 5,596,668 A | 1/1997 | DiGiovanni et al. |
| 5,602,677 A | 2/1997 | Tournois |
| 5,617,434 A | 4/1997 | Tamura et al. |
| 5,627,848 A | 5/1997 | Fermann et al. |
| 5,633,750 A | 5/1997 | Nogiwa et al. |
| 5,633,885 A | 5/1997 | Galvanauskas et al. |
| 5,656,186 A | 8/1997 | Mourou et al. |
| 5,663,731 A | 9/1997 | Theodoras, II et al. |
| 5,677,769 A | 10/1997 | Bendett |
| 5,689,519 A | 11/1997 | Fermann et al. |
| 5,696,782 A | 12/1997 | Harter et al. |
| 5,701,319 A | 12/1997 | Fermann |
| 5,703,639 A | 12/1997 | Farrier et al. |
| 5,708,669 A | 1/1998 | DiGiovanni et al. |
| 5,710,424 A | 1/1998 | Thoedoras, II et al. |
| 5,720,894 A | 2/1998 | Neev et al. |
| 5,726,855 A | 3/1998 | Mourou et al. |
| 5,778,016 A | 7/1998 | Sucha et al. |
| 5,788,688 A | 8/1998 | Bauer et al. |
| 5,818,630 A | 10/1998 | Fermann et al. |
| 5,822,097 A | 10/1998 | Tournois |
| 5,847,863 A | 12/1998 | Galvanauskas et al. |
| 5,862,287 A | 1/1999 | Stock et al. |
| 5,867,304 A | 2/1999 | Galvanauskas et al. |
| 5,875,408 A | 2/1999 | Bendett et al. |

(Continued)

FOREIGN PATENT DOCUMENTS

JP    2003181661 A    7/2003

(Continued)

OTHER PUBLICATIONS

U.S. Appl. No. 10/916,368, Richard Stoltz, Pulse Energy Adjustment for Changes in Ablation Spot Size, filed Aug. 11, 2004.

(Continued)

*Primary Examiner*—A. Farah
(74) *Attorney, Agent, or Firm*—Carr & Ferrell LLP

(57) ABSTRACT

The present invention includes a method of surgical material removal from a body by optical-ablation with controlled pulse energy from an amplifier including inputting an ablation-threshold-pulse-energy-for-material-being-ablated signal; controlling the energy of a pulse and the pulse repetition rate and by knowing the type of material being removed, the system can control the removal to predetermined rate and, thus knowing the removal rate, it can know how long to run to stop at the predetermined volume.

16 Claims, No Drawings

U.S. PATENT DOCUMENTS

| | | | |
|---|---|---|---|
| 5,880,823 | A | 3/1999 | Lu |
| 5,880,877 | A | 3/1999 | Fermann et al. |
| 5,898,485 | A | 4/1999 | Nati, Jr. |
| 5,920,668 | A | 7/1999 | Uehara et al. |
| 5,923,686 | A | 7/1999 | Fermann et al. |
| 5,936,716 | A | 8/1999 | Pinsukanjana et al. |
| 6,014,249 | A | 1/2000 | Fermann et al. |
| 6,020,591 | A | 2/2000 | Harter et al. |
| 6,034,975 | A | 3/2000 | Harter et al. |
| 6,061,373 | A | 5/2000 | Brockman et al. |
| 6,072,811 | A | 6/2000 | Fermann et al. |
| 6,075,588 | A | 6/2000 | Pinsukanjana et al. |
| 6,081,369 | A | 6/2000 | Waarts et al. |
| 6,120,857 | A | 9/2000 | Balooch et al. |
| 6,130,780 | A | 10/2000 | Joannopoulos et al. |
| 6,151,338 | A | 11/2000 | Grubb et al. |
| 6,154,310 | A | 11/2000 | Galvanauskas et al. |
| 6,156,030 | A * | 12/2000 | Neev ............................ 606/10 |
| 6,181,463 | B1 | 1/2001 | Galvanauskas et al. |
| 6,198,568 | B1 | 3/2001 | Galvanauskas et al. |
| 6,208,458 | B1 | 3/2001 | Galvanauskas et al. |
| 6,249,630 | B1 | 6/2001 | Stock et al. |
| 6,252,892 | B1 | 6/2001 | Jiang et al. |
| 6,256,328 | B1 | 7/2001 | Delfyett et al. |
| 6,269,108 | B1 | 7/2001 | Tabirian et al. |
| 6,275,512 | B1 | 8/2001 | Fermann |
| 6,303,903 | B1 | 10/2001 | Liu |
| 6,314,115 | B1 | 11/2001 | Delfyett et al. |
| 6,327,074 | B1 | 12/2001 | Bass et al. |
| 6,327,282 | B2 | 12/2001 | Hammons et al. |
| 6,334,011 | B1 | 12/2001 | Galvanauskas et al. |
| 6,335,821 | B1 | 1/2002 | Suzuki et al. |
| RE37,585 | E | 3/2002 | Mourou et al. |
| 6,355,908 | B1 | 3/2002 | Tatah et al. |
| 6,362,454 | B1 | 3/2002 | Liu |
| 6,365,869 | B1 | 4/2002 | Swain et al. |
| 6,404,944 | B1 | 6/2002 | Wa et al. |
| 6,421,169 | B1 | 7/2002 | Bonnedal et al. |
| 6,433,303 | B1 | 8/2002 | Liu et al. |
| 6,433,305 | B1 | 8/2002 | Liu et al. |
| 6,433,760 | B1 | 8/2002 | Vaissie et al. |
| 6,501,590 | B2 | 12/2002 | Bass et al. |
| 6,522,460 | B2 | 2/2003 | Bonnedal et al. |
| 6,525,873 | B2 | 2/2003 | Gerrish et al. |
| 6,526,327 | B2 | 2/2003 | Kar et al. |
| 6,529,319 | B2 | 3/2003 | Youn et al. |
| 6,549,547 | B2 | 4/2003 | Galvanauskas et al. |
| 6,567,431 | B2 | 5/2003 | Tabirian et al. |
| 6,573,813 | B1 | 6/2003 | Joannopoulos et al. |
| 6,574,024 | B1 | 6/2003 | Liu |
| 6,576,917 | B1 | 6/2003 | Silfvast |
| 6,580,553 | B2 | 6/2003 | Kim et al. |
| 6,597,497 | B2 | 7/2003 | Wang et al. |
| 6,603,911 | B2 | 8/2003 | Fink et al. |
| 6,621,045 | B1 | 9/2003 | Liu et al. |
| 6,627,844 | B2 | 9/2003 | Liu et al. |
| 6,642,477 | B1 | 11/2003 | Patel et al. |
| 6,647,031 | B2 | 11/2003 | Delfyett et al. |
| 6,654,161 | B2 | 11/2003 | Bass et al. |
| 6,661,816 | B2 | 12/2003 | Delfyett et al. |
| 6,671,298 | B1 | 12/2003 | Delfyett et al. |
| 6,690,686 | B2 | 2/2004 | Delfyett et al. |
| 6,710,288 | B2 | 3/2004 | Liu et al. |
| 6,710,293 | B2 | 3/2004 | Liu et al. |
| 6,711,334 | B2 | 3/2004 | Szkopek et al. |
| 6,720,519 | B2 | 4/2004 | Liu et al. |
| 6,723,991 | B1 | 4/2004 | Sucha et al. |
| 6,728,439 | B2 | 4/2004 | Weisberg et al. |
| 6,735,229 | B1 | 5/2004 | Delfyett et al. |
| 6,738,144 | B1 | 5/2004 | Dogariu |
| 6,744,555 | B2 | 6/2004 | Galvanauskas et al. |
| 6,749,285 | B2 | 6/2004 | Liu et al. |
| 6,774,869 | B2 | 8/2004 | Biocca et al. |
| 6,782,207 | B1 | 8/2004 | Efimov |
| 6,787,734 | B2 | 9/2004 | Liu |
| 6,788,864 | B2 | 9/2004 | Ahmad et al. |
| 6,791,060 | B2 | 9/2004 | Dunsky et al. |
| 6,801,551 | B1 * | 10/2004 | Delfyett et al. ............... 372/23 |
| 6,803,539 | B2 | 10/2004 | Liu et al. |
| 6,804,574 | B2 | 10/2004 | Liu et al. |
| 6,807,375 | B2 | 10/2004 | Dogariu |
| 6,815,638 | B2 | 11/2004 | Liu |
| 6,819,694 | B2 | 11/2004 | Jiang et al. |
| 6,819,837 | B2 | 11/2004 | Li et al. |
| 6,822,251 | B1 | 11/2004 | Arenberg et al. |
| 6,829,517 | B2 | 12/2004 | Cheng et al. |
| 6,878,900 | B2 | 4/2005 | Corkum et al. |
| 6,897,405 | B2 | 5/2005 | Cheng et al. |
| 6,928,490 | B1 | 8/2005 | Bucholz et al. |
| 7,022,119 | B2 | 4/2006 | Hohla |
| 7,143,769 | B2 * | 12/2006 | Stoltz et al. ................ 128/898 |
| 7,217,266 | B2 | 5/2007 | Anderson et al. |
| 2002/0176676 | A1 | 11/2002 | Johnson et al. |
| 2003/0060808 | A1 | 3/2003 | Wilk |
| 2003/0161378 | A1 | 8/2003 | Zhang et al. |
| 2004/0231682 | A1 * | 11/2004 | Stoltz et al. ................ 128/898 |
| 2005/0035097 | A1 | 2/2005 | Stoltz |
| 2005/0038487 | A1 * | 2/2005 | Stoltz ........................... 607/88 |
| 2005/0061779 | A1 | 3/2005 | Blumenfeld et al. |
| 2005/0065502 | A1 * | 3/2005 | Stoltz ............................. 606/9 |
| 2005/0074974 | A1 | 4/2005 | Stoltz |
| 2005/0077275 | A1 | 4/2005 | Stoltz |
| 2005/0127049 | A1 | 6/2005 | Woeste et al. |
| 2005/0167405 | A1 * | 8/2005 | Stoltz et al. ............ 219/121.62 |
| 2005/0171516 | A1 * | 8/2005 | Stoltz et al. .................... 606/9 |
| 2005/0171518 | A1 | 8/2005 | Stoltz et al. |
| 2005/0177143 | A1 * | 8/2005 | Bullington et al. ........... 606/10 |
| 2005/0195726 | A1 | 9/2005 | Bullington et al. |
| 2006/0064079 | A1 * | 3/2006 | Stoltz et al. .................. 606/10 |
| 2006/0067604 | A1 | 3/2006 | Bull et al. |

FOREIGN PATENT DOCUMENTS

| | | |
|---|---|---|
| WO | WO 2004/105100 A2 | 12/2004 |
| WO | WO 2004/114473 A2 | 12/2004 |
| WO | WO 2005/018060 A2 | 2/2005 |
| WO | WO 2005/018061 A2 | 2/2005 |
| WO | WO 2005/018062 A2 | 2/2005 |
| WO | WO 2005/018063 A2 | 2/2005 |

OTHER PUBLICATIONS

U.S. Appl. No. 10/850,325, Richard Stoltz, Controlling Temperature of an Optical Amplifier by Controlling Pump Diode Current, filed May 19, 2004.

U.S. Appl. No. 11/057,867, Michael Marshall Mielke, Method of Generating an Ultra-Short Pulse Using a High-Frequency Ring Oscillator, filed Feb. 13, 2005.

U.S. Appl. No. 11/057,868, Michael Marshall Mielke, Amplifying of high Energy Laser Pulses, filed Feb. 13, 2005.

U.S. Appl. No. 11/224,867, Peter Delfyett, Laser Ablation Method and Apparatus Having a Feedback Loop and Control Unit, filed Sep. 12, 2005.

U.S. Appl. No. 11/233,634, James F. Brennan, III, Wavelength-Stabilized Pump Diodes for Pumping Gain Media in an Ultrashort Pulsed Laser System, filed Sep. 22, 2005.

U.S. Appl. No. 11/112,256, James F. Brennan, III, Bragg Fibers in Systems for the Generation of High Peak Power Light, filed Apr. 22, 2005.

U.S. Appl. No. 11/229,302, Michael Marshall Mielke, Actively Stabilized Systems for the Generation of Ultrashort Optical Pulses, filed Sep. 15, 2005.

Yeh et al., "Theory of Bragg Fiber", Journal of the Optical Society America, Sep. 1978, pp. 1196, vol. 68, No. 9.

Engeness et al., "Dispersion Tailoring and Compensation by Modal Interations in Omniguide Fibers," Optics Express, May 19, 2003, pp. 1175-1196, vol. 11, No. 10.

Fink et al., "Guiding Optical Light in Air Using an All-Dielectric Structure," Journal of Lightwave Technology, Nov. 1999, pp. 2039-2041, vol. 17, No. 11.

Siegman, "Unstable Optical Resonators", Applied Optics, Feb. 1974, pp. 353-367, vol. 13, No. 2.

Koechner, "Solid State Laser Engineering", Oct. 29, 1999, Section 5.5, pp. 270-277, 5th Edition, Springer.

Chen et al. "Dispersion-Managed Mode Locking", Journal of the Optical Society of America B, Nov. 1999, pp. 1999-2004, vol. 16, No. 11, Optical Society of America.

Resan et al. "Dispersion-Managed Semiconductor Mode-Locked Ring Laser", Optics Letters, Aug. 1, 2003, pp. 1371-1373, vol. 28, No. 15, Optical Society of America.

Dasgupta, S. et al., "Design of Dispersion-Conpensating Bragg Fiber with an Ultrahigh Figure of Merit," Optics Letters, Aug. 1, 2005, vol. 30, No. 15, Optical Society of America.

Mohammed, W. et al., "Selective Excitation of the TE01 Mode in Hollow-Glass Waveguide Using a Subwavelength Grating," IEEE Photonics Technology Letters, Jul. 2005, vol. 17, No. 7, IEEE.

Delfyett, P et al., "Ultrafast Semiconductor Laser-Diode-Seeded Cr:LiSAF Rengerative Amplifier System", Applied Optics, May 20, 1997, pp. 3375-3380, vol. 36, No. 15, Octoical Society of America.

Levy et al., "Engineering Space-Variant INhomogeneous Media for Polarization Control," Optics Letters, Aug. 1, 2004, pp. 1718-1720, vol. 29, No. 15, Optical Society of America.

Ibanescu et al., "Analysis of Mode Structure in Hollow Dielectric Waveguide Fibers," Physical Review E 67, 2003, The American Physical Society.

\* cited by examiner

ABLATIVE MATERIAL REMOVAL WITH A PRESET REMOVAL RATE OR VOLUME OR DEPTH

CROSS-REFERENCE TO RELATED APPLICATIONS

This application claims priority to U.S. Provisional Patent Application Ser. No. 60/494,273, entitled "Ablative Material Removal With A Preset Removal Rate or Volume or Depth," filed Aug. 11, 2003, and U.S. Provisional Patent Application Ser. No. 60/503,578, entitled "Controlling Optically-Pumped Optical Pulse Amplifiers," filed Sep. 17, 2003.

TECHNICAL FIELD OF THE INVENTION

The present invention relates in general to the field of light amplification and, more particularly to the ablative material removal using a preset removal rate or volume or depth.

BACKGROUND OF THE INVENTION

Ablative material removal is especially useful for medical purposes, either in-vivo or on the outside surface (e.g., skin or tooth), as it is essentially non-thermal and generally painless. Ablative removal of material is generally done with a short optical pulse that is stretched, amplified and then compressed. A number of types of laser amplifiers have been used for the amplification.

Laser machining can remove ablatively material by dis-associate the surface atoms and melting the material. Laser ablation is done efficiently with a beam of short pulses (generally a pulse-duration of three picoseconds or less). Techniques for generating these ultra-short pulses (USP) are described, e.g., in a book entitled "Femtosecond Laser Pulses" (C. Rulliere, editor), published 1998, Springer-Verlag Berlin Heidelberg New York. Generally large systems, such as Ti:Sapphire, are used for generating ultra-short pulses (USP).

USP phenomenon was first observed in the 1970's, when it was discovered that mode-locking a broad-spectrum laser could produce ultra-short pulses. The minimum pulse duration attainable is limited by the bandwidth of the gain medium, which is inversely proportional to this minimal or Fourier-transform-limited pulse duration. Mode-locked pulses are typically very short and will spread (i.e., undergo temporal dispersion) as they traverse any medium. Subsequent pulse-compression techniques are often used to obtain USP's. Pulse dispersion can occur within the laser cavity so that compression techniques are sometimes added intra-cavity. When high-power pulses are desired, they are intentionally lengthened before amplification to avoid internal component optical damage. This is referred to as "Chirped Pulse Amplification" (CPA). The pulse is subsequently compressed to obtain a high peak power (pulse-energy amplification and pulse-duration compression).

SUMMARY OF THE INVENTION

Ablative material removal with a short optical pulse is especially useful for medical purposes and can be done either in-vivo or on the body surface (e.g., skin or tooth), as it is essentially non-thermal and generally painless. One embodiment, the removal volume or depth for ablative material removal is preset. In one embodiment, the pulse energy density applied to the body is between 2.5 and 3.6 times ablation threshold of the body portion being ablated, whereby a relatively constant removal per pulse is accomplished. In one embodiment, the pulse energy density is controlled by controlling pulse energy, whereby it is much more convenient than changing the ablation spot size. In one embodiment, material removal at a predetermined rate and/or stop at a predetermined volume or depth is accomplished by controlling the energy of a pulse and the pulse repetition rate for the type of material being removed.

In one embodiment, the total volume to be removed is known. In other embodiments a certain volume is removed and inspect before proceeding. In either case it is convenient to have a system that removes a predetermined volume. In one embodiment, the control of pulse energy allows a reasonably accurate volume removal per pulse, other embodiment may combine this with a controlled repetition rate allowing a reasonably accurate volume removal per unit of time. One embodiment, the invention controls the removal of material to predetermined rate through controlling the energy of a pulse and the pulse repetition rate, e.g., as described above, and by knowing the type of material being removed, thus, knowing the removal rate, it can know how long to run to stop at the predetermined volume.

Materials are most efficiently removed at pulse energy densities about three times the materials ablation threshold, and as materials ablate at different thresholds, efficient operation requires control of the pulse energy density. Typically in surgery, the ablation has a threshold of less than 1 Joule per square centimeter, but occasionally surgical removal, especially of foreign material, may require dealing with an ablation threshold of up to about 2 Joules per square centimeter. In one embodiment, the pulse energy densities are controlled at three times the materials ablation threshold. Control of pulse energy also allows reasonably accurate volume removal per pulse, which combined with a controlled repetition rate, allows reasonably accurate volume removal per unit of time. Pulse energy density can be controlled through controlling the pulse energy. In one embodiment, controlling pulse repetition rate of a fiber amplifiers operating at high repetition rates can be controled by optical pumping power or pulse energy. In one embodiment, the invention is fine-tuning by controlling optical pumping power.

In one embodiment, the ablation rate is controllable independent of pulse energy. The use of two or more amplifier in parallel a train mode (pulses from one amplifier being delayed to arrive one or more nanoseconds after those from another amplifier) allows step-wise control of ablation rate independent of pulse energy density. In one embodiment, step-wise control of ablation rate independent of pulse energy density is accomplished using two or more amplifier in parallel a train mode. At lower desired ablation rates, one or more amplifiers can be shut down. The use of parallel amplifiers in a train-mode in either type of system provides faster ablation, while providing greater cooling surface area to minimize thermal problems. In one embodiment, one or more of the parallel amplifiers can be shut down.

One embodiment of the present invention is a method of the of material removal from a body by optical-ablation with controlled pulse energy from a fiber amplifier, including inputting an ablation-threshold-pulse-energy-for-material-being-ablated signal; utilizing an optical oscillator in the generation of a series of wavelength-swept-with-time pulses; primarily controlling pulse energy based on the ablation-threshold-pulse-energy-for-material-being-ablated signal by either selecting pulses from the oscillator generated series of wavelength-swept-with-time pulses, wherein the fraction of pulses selected can be controllably varied to give a selected pulse repetition rate that is a fraction of the oscillator repetition rate, or passing electrical current through at least one pump diode to generate pumping light, optically pumping the fiber amplifier with the pumping light, and controlling pump diode current; amplifying the wavelength-swept-with-time pulse with the fiber-amplifier; time-compressing the amplified pulse and illuminating a portion of the body with the time-compressed optical pulse, whereby the volumetric removal rate can be determined from the pulse energy and the ablation-threshold-pulse-energy-for-material-being-ablated signal.

In one embodiment, the volume of material to be ablated is inputted and ablation is performed for a length of time to remove that volume. In another embodiment, the depth of material to be ablated is inputted and ablation is performed for a length of time to remove material to that depth at the determined volumetric removal rate.

One embodiment uses a fiber-amplifier or other optical amplifier (e.g., a Cr:YAG amplifier) and air-path between gratings compressor, e.g., with the amplified pulses between ten picoseconds and one nanosecond. One embodiment, uses an erbium-doped fiber amplifier, and the air-path between gratings compressor preferably is a Tracey grating compressor. Another embodiment uses a chirped fiber compressor combination, e.g., with the initial pulses between 1 and 20 nanoseconds. In one embodiment, two or more fiber-amplifier are used in parallel, or two or more semiconductor optical amplifiers are used in parallel. In one embodiment one or more amplifiers are used with one compressor.

High ablative pulse repetition rates are preferred and the total pulses per second (the total system repetition rate) from the one or more parallel optical amplifiers is preferably greater than 0.6 million. In one embodiment, the ablative pulse repetition rate totals 0.6 or greater million pulses per second.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Ablative material removal with a short optical pulse is especially useful for medical purposes and can be done either in-vivo or on the body surface and ablative material removal with a preset removal volume is sometimes desirable. Control of pulse energy density (preferably the ablation spot has an essentially fixed area, and thus controlling pulse energy controls pulse energy density) in the ablation spot for optimum removal efficiency is not only desirable for efficiency's sake, but also gives a knowable removal per pulse. One embodiment controls the energy of a pulse and the pulse repetition rate to control the removal to predetermined rate and/or stop at a predetermined volume. Typically, the ablation has a threshold of less than 1 Joule per square centimeter, but occasionally surgical removal of foreign material may require dealing with an ablation threshold of up to about 2 Joules per square centimeter. Some materials ablate much faster than others and control of the ablation rate is desirable. Control of pulse energy density in the ablation spot for optimum removal efficiency is therefore, desirable. In one embodiment, the pulse density of a fiber amplifier is controlled step-wise by controlling repetition rate, and in another embodiment, the pulse density controlled or fine-tuned by controlling optical pumping power. One embodiment uses 1550 nm light.

In one embodiment, the ablation rate is controlled independent of pulse energy. One embodiment uses two or more amplifiers in train mode (pulses from one amplifier being delayed to arrive one or more nanoseconds after those from another amplifier) to step-wise control the ablation rate independent of pulse energy. In embodiments desiring lower desired ablation rates, one or more amplifiers are shut off (e.g., the optical pumping to the fiber amplifier shut off), and there will be fewer pulses per train. In one embodiment, 20 amplifiers produce a maximum of 20 pulses in a train, and in other embodiments three or four amplifiers are used to produce three or four pulses per train. Alternately, while continuous wave (CW) operation might generally be used in operating amplifiers, amplifiers might be run in a staggered fashion, e.g., on for a first period and then turned off for one second period, and a first period dormant amplifier turned on during the second period, and so forth, to spread the heat load. In one embodiment, two or more amplifiers are configured to run in a staggered fashion. In one embodiment having a known type of material being removed, the removal to predetermined rate is accomplished by controlling the energy of a pulse and the pulse repetition rate, whereby knowing the removal rate the system can automatically stop when the predetermined volume is removed. If the area of removal is fixed during the ablation and the removal rate is known, the system can automatically stop when material has been removed to a predetermined depth.

One embodiment includes a fiber-amplifier and a compressor allowing the invention to be man-portable. As used herein, the term "man-portable" can mean capable of being moved reasonably easily by one person, e.g., as wheeling a wheeled cart from room to room or possibly even being carried in a backpack.

One embodiment includes the removal of material from a body by optical-ablation with controlled pulse energy from a fiber amplifier, including inputting an ablation-threshold-pulse-energy-for-material-being-ablated signal; utilizing an optical oscillator in the generation of a series of wavelength-swept-with-time pulses; primarily controlling pulse energy based on the ablation-threshold-pulse-energy-for-material-being-ablated signal by either selecting pulses from the oscillator generated series of wavelength-swept-with-time pulses, wherein the fraction of pulses selected can be controllably varied to give a selected pulse repetition rate that is a fraction of the oscillator repetition rate, or passing electrical current through at least one pump diode to generate pumping light, optically pumping the fiber amplifier with the pumping light, and controlling pump diode current; using an ablation spot-size sensor to measure the ablation spot size and dynamically adjusting either the fraction of pulses selected or the pump diode current for changes in ablation spot size from the nominal spot size; amplifying the wavelength-swept-with-time pulse with the fiber-amplifier; time-compressing the amplified pulse and illuminating a portion of the body with the time-compressed optical pulse, whereby controlling the pulse selection and/or the pump diode controls the pulse energy; and determining a volumetric removal rate from the pulse energy and the ablation-threshold-pulse-energy-for-material-being-ablated signal. Preferably, a volume of material to be ablated is inputted and ablation is performed for a length of time to remove that volume at the volumetric removal rate.

In one embodiment, the inputting of an ablation-threshold-pulse-energy-for-material-being-ablated signal is by a selector switch, whereby the selector switch is used to directly or indirectly select a volume removal per pulse level. In one embodiment, the average pulse energy is between about 2.5 and about 3.6 times the ablation threshold. Another embodiment uses a multi-position selector switch to indicate classes of materials, whereby setting the switch to one of those classes results in the selection. In one embodiment, the volume removed per pulse is related to the ablation threshold. In one embodiment an indexed switch is used to select one of two or more levels of volume removed per pulse.

In one embodiment, the ablation probe is mounted on an x-y-z-positioner. In another embodiment, the probe is moved in the z-direction to follow surfaces. One embodiment, scans an ablation area by moving the beam without moving the probe. Another embodiment scans a larger area by moving the beam over a first area, and then stepping the probe to second portion of the large area and then scanning the beam over the second area, and so on.

In one embodiment, the initial pulse is amplified by a fiber-amplifier (e.g., a erbium-doped fiber amplifier or EDFA) and compressed by an air-path between gratings compressor (e.g., a Tracey grating compressor), with the compression creating a sub-picosecond ablation pulse to produce a initial pulses of between about 10 picoseconds and about one nanosecond. Another embodiment uses a semiconductor optical amplifier (SOA) and with a chirped fiber compressor. Generally, a semiconductor optical amplifier produces a pulse of between about 1 and 20 nanosecond during amplification. One embodiment uses a semiconductor generated initial pulse and a SOA preamplifier to amplify the initial pulse before introduction into the fiber amplifier.

While the compressors in either type of system can be run with inputs from more than one amplifier, reflections from the parallel amplifiers can cause a loss of efficiency, and thus should be minimized. The loss is especially important if the amplifiers are amplifying signals at the same time, as is the case with the SOAs. In one embodiment each of the parallel SOAs has its own compressor, whereby the amplified pulses may be put into a single fiber after the compressors, reducing greatly the reflections from the joining (e.g., in a star connector). Fiber amplifiers allow a nanosecond spacing of sub-nanosecond pulses minimizes amplifying of multiple signals at the same time, and a single compressor is used. In one embodiment multiple fiber amplifiers are used with a single compressor.

Fiber amplifiers have a storage lifetime of about 100 to 300 microseconds and for ablations purposes, fiber amplifiers have generally been operated with a time between pulses of equal to or greater than the storage lifetime, and thus are generally run a repetition rate of less than 3-10 kHz. Fiber amplifiers are available with average power of 30 W or more. In one embodiment a moderate-power 5 W average power fiber amplifiers is operated to produce a pulses of 500 or more microjoules. In one embodiment, energy densities above the ablation threshold are needed for non-thermal ablation, and increasing the energy in such a system, increases the ablation rate in either depth or allows larger areas of ablation or both. One embodiment, run a fiber amplifier with a time between pulses of a fraction (e.g., one-half or less) of the storage lifetime and use a smaller ablation spot. In one embodiment, the spot is about 50 microns or less in diameter, and other embodiments allow a smaller spot to be scanned to get a larger effective ablation area.

One embodiment increases the ablation rate by increasing the effective repetition rate using parallel fiber amplifiers to generate a train of pulses, wherein thermal problems are avoided and controlling the ablation rate using a lesser number of operating fiber amplifiers. One embodiment uses a SOA preamplifier to amplify the initial pulse before splitting to drive multiple parallel fiber amplifiers and another SOA before the introduction of the signal into each fiber amplifier, whereby individual fiber amplifiers can be shut down rapidly.

One embodiment uses a 1 ns pulse with a fiber amplifier and air optical-compressor (e.g., a Tracey grating compressor) giving a compression with ~40% losses. At less than 1 ns, the losses in a Tracey grating compressor are generally lower. If the other-than-compression losses are about 10%, 2 nanoJoules are needed from the amplifier to get 1 nanoJoule on the target. The use of greater than 1 ns pulses in an air optical-compressor presents two problems; the difference in path length for the extremes of long and short wavelengths needs to be about three cm or more and thus the compressor is large and expensive, and the losses increase with a greater degree of compression.

In another embodiment, a semiconductor optical amplifier (SOA) and a chirped fiber compressor, with pulses of between about 1 and about 20 nanosecond during amplification are run at repetition rates with a time between pulses of the semiconductor storage lifetime or more. In one embodiment, a semiconductor generated initial sub-picosecond pulse and a SOA preamplifier is used to amplify the initial pulse before splitting to drive multiple SOAs. In one embodiment, a smaller ablation spot is scanned to increase the effective ablation area. One embodiment uses parallel SOAs to generate a train of pulses to increase the ablation rate by further increasing the effective repetition rate, wherein thermal problems are avoided and ablation rate is controlled by the use of a lesser number of operating SOAs. One embodiment operates with pulse energy densities at about three times the ablation threshold.

Ablative material removal is especially useful for medical purposes either "in-vivo" or on the body surface and typically has an ablation threshold of less than 1 Joule per square centimeter, but may occasionally require surgical removal of foreign material with an ablation threshold of up to about 2 Joules per square centimeter. One embodiment uses two or more amplifiers in parallel train mode, whereby pulses from one amplifier being delayed to arrive one or more nanoseconds after those from another amplifier. At lower desired powers, one or more amplifiers can be shut off (e.g., the optical pumping to a fiber amplifier), and there will be fewer pulses per train. One embodiment includes 20 amplifiers producing a maximum of 20 pulses in a train, however other embodiments can use three or four amplifiers and produce three or four pulses per train.

Generally, the fiber amplifiers are optically-pumped continuous wave (CW) (and are amplifying perhaps 100,000 times per second in 1 nanosecond pulses). Alternately, non-CW-pumping might be used in operating amplifiers, with amplifiers run in a staggered fashion, e.g., one on for a first half-second period and then turned off for a second half-second period, and another amplifier, dormant during the first-period, turned on during the second period, and so forth, to spread the heat load. In one embodiment, the amplifiers are optically-pumped CW. In other embodiments the amplifiers are non-CW-pumped.

One embodiment controls the input optical signal power, optical pumping power of fiber amplifiers, timing of input pulses, length of input pulses, and timing between start of optical pumping and start of optical signals to control pulse power, and average degree of energy storage in fiber.

In one embodiment, the oscillator, amplifier and compressor are within a man-portable system, and/or the compression is done in an air-path between gratings compressor. In one embodiment, the compressed optical pulse has a sub-picosecond duration, and the oscillator pulse has a duration between about 10 picoseconds and about one nanosecond. In one embodiment, ablation is preformed from an outside surface of the body and another embodiment ablation is done inside the body. In some embodiments, one or more amplifiers are used in a mode where amplified pulses from one amplifier are delayed to arrive one or more nanoseconds after those from any other amplifier, to allow control of ablation rate independent of pulse energy. In one embodiment, the pulse energy applied to the body is between about 2.5 and 3.6 times ablation threshold of the body portion being ablated, whereby a relatively constant removal per pulse is achieved. Preset removal rate, as used herein includes controlling the removal per pulse by controlling the pulse energy to give a pulse energy density between 2.5 and 3.6 times ablation threshold for the spot size.

One embodiment uses a fiber amplifiers have a maximum power of 4 MW, and thus a 10-microJoule ablation pulse could be as short as 2 ps. Thus a 10 ps, 10 microjoule pulse, at 500 kHz (or 50 microjoule with 100 kHz). In one embodiment, two or more amplifiers are operated in a train mode and switching fiber amplifiers. In one embodiment, the running of ten fiber amplifiers are rotated such that only five are operating at any one time (e.g., each on for $1/10^{th}$ of a second and off for $1/10^{th}$ of a second). One embodiment, has ten fiber amplifiers with time spaced inputs, e.g., by 1 ns, to give a train of one to 10 pulses. In one embodiment, 5 W amplifiers operating at 100 kHz (and e.g., 50 microjoules) are stepped between 100 kHz and 1 MHz. With 50% post-amplifier optical efficiency and 50 microjoules, to get 6 J/sq. cm on the target, the spot size would be about 20 microns.

Another embodiment has 20 fiber amplifiers with time spaced inputs, by 1 ns, to give a train of one to 20 pulses. With 5 W amplifiers operating at 50 kHz (and e.g., 100 microjoules) this could step between 50 kHz and 1 MHz. With 50% post-amplifier optical efficiency and 100 microjoules, to get 6 J/sq. cm on the target, the spot size would be about 33 microns. In one embodiment, the amplified pulse is about 50 to about 100 picoseconds long. Another embodiment having 10 fiber amplifiers can step between 50 kHz and 500 kHz.

Another embodiment has 5 W amplifiers operating at 20 kHz (and e.g., 250 microjoules) with 10 fiber amplifiers and can step between 20 kHz and 200 kHz. With 50% post-amplifier optical efficiency and 250 microjoules, to get 6 J/sq. cm on the target, the spot size would be about 50 microns. The amplified pulse is about 100 to about 250 picoseconds long. Another embodiment having 30 fiber amplifiers can step between 20 kHz and 600 kHz.

Generally, the pulse generator controls the input repetition rate of the fiber amplifiers to tune energy per pulse to about three times threshold per pulse. In one embodiment, the pulse generator controls the input repetition rate of the fiber amplifiers. Another embodiment generates a sub-picosecond pulse and time-stretching the pulse within semiconductor pulse generator to give the initial wavelength-swept-with-time initial pulse.

One embodiment measures light leakage from the delivery fiber to get a feedback proportional to pulse power and/or energy for control purposes. One embodiment measures the spot size with a video camera. In one embodiment, the measurement is with a stationary spot, and another embodiment uses a linear scan.

In one embodiment a camera is used (see "Camera Containing Medical Tool" provisional application No. 60/472,071; filed May 20, 2003; which is incorporated by reference herein) including an optical fiber in a probe to convey an image back to a vidicon-containing remote camera body. In one embodiment, the camera is used "in-vivo." One embodiment uses a handheld beam-emitting probe.

Smaller ablation areas may be scanned by moving the beam without moving the probe. Large areas may be scanned by moving the beam over a first area, and then stepping the probe to second portion of the large area and then scanning the beam over the second area, and so on. One embodiment scans the beam over an area without moving the probe. One embodiment scans the beam over a first area, and then stepping the probe to second portion of the large area and then scanning the beam over the second area. One embodiment includes a beam deflecting mirrors mounted on piezoelectric actuators (see "Scanned Small Spot Ablation With A High-Rep-Rate" U.S. Provisional Patent Applications, Ser. No. 60/471,972, filed May 20, 2003; which is incorporated by reference herein). In one embodiment, the actuators scan over a larger region but with the ablation beam only enabled to ablate portions having the defined color and/or area. One embodiment allows evaluation after a prescribed time through a combination of preset time and, area and/or colors.

Information of such a system and other information on ablation systems are given in co-pending provisional applications listed in the following paragraphs (which are also at least partially co-owned by, or exclusively licensed to, the owners hereof) and are hereby incorporated by reference herein (provisional applications listed by docket number, title and provisional number):

"Laser Machining" U.S. Provisional Patent Applications, Ser. No. 60/471,922; "Camera Containing Medical Tool" U.S. Provisional Patent Applications, Ser. No. 60/472,071; "Scanned Small Spot Ablation With A High-Rep-Rate" U.S. Provisional Patent Applications, Ser. No. 60/471,972; and "Stretched Optical Pulse Amplification and Compression", U.S. Provisional Patent Applications, Ser. No. 60/471,971, were filed May 20, 2003;

"Controlling Repetition Rate Of Fiber Amplifier" Ser. No. 60/494,102; "Controlling Pulse Energy Of A Fiber Amplifier By Controlling Pump Diode Current" U.S. Provisional Patent Applications, Ser. No. 60/494,275; "Pulse Energy Adjustment For Changes In Ablation Spot Size" U.S. Provisional Patent Applications, Ser. No. 60/494,274; "Fiber Amplifier With A Time Between Pulses Of A Fraction Of The Storage Lifetime"; "Man-Portable Optical Ablation System" U.S. Provisional Patent Applications, Ser. No. 60/494,321; "Controlling Temperature Of A Fiber Amplifier By Controlling Pump Diode Current" U.S. Provisional Patent Applications, Ser. No. 60/494,322; "Altering The Emission Of An Ablation Beam for Safety or Control" U.S. Provisional Patent Applications, Ser. No. 60/494,267;

"Enabling Or Blocking The Emission Of An Ablation Beam Based On Color Of Target Area" U.S. Provisional Patent Applications, Ser. No. 60/494,172; "Remotely-Controlled Ablation of Surfaces" Ser. No. 60/494,276 and "Ablation Of A Custom Shaped Area" U.S. Provisional Patent Applications, Ser. No. 60/494,180; were filed Aug. 11, 2003. "High-Power-Optical-Amplifier Using A Number Of Spaced, Thin Slabs" U.S. Provisional Patent Applications, Ser. No. 60/497,404 was filed Aug. 22, 2003;

"Spiral-Laser On-A-Disc", U.S. Provisional Patent Applications, Ser. No. 60/502,879; and partially "Laser Beam Propagation in Air", U.S. Provisional Patent Applications, Ser. No. 60/502,886 were filed on Sep. 12, 2003. "Active Optical Compressor" U.S. Provisional Patent Applications, Ser. No. 60/503,659 filed Sep. 17, 2003;

"High Power SuperMode Laser Amplifier" U.S. Provisional Patent Applications, Ser. No. 60/505,968 was filed Sep. 25, 2003, "Semiconductor Manufacturing Using Optical Ablation" U.S. Provisional Patent Applications, Ser. No. 60/508,136 was filed Oct. 2, 2003, "Composite Cutting With Optical Ablation Technique" U.S. Provisional Patent Applications, Ser. No. 60/510,855 was filed Oct. 14, 2003 and "Material Composition Analysis Using Optical Ablation", U.S. Provisional Patent Applications, Ser. No. 60/512,807 was filed Oct. 20, 2003;

"Quasi-Continuous Current in Optical Pulse Amplifier Systems" U.S. Provisional Patent Applications, Ser. No. 60/529,425 and "Optical Pulse Stretching and Compressing" U.S. Provisional Patent Applications, Ser. No. 60/529,443, were both filed Dec. 12, 2003;

"Start-up Timing for Optical Ablation System" U.S. Provisional Patent Applications, Ser. No. 60/539,026; "High-Frequency Ring Oscillator", U.S. Provisional Patent Applications, Ser. No. 60/539,024; and "Amplifying of High Energy Laser Pulses", U.S. Provisional Patent Applications, Ser. No. 60/539,025; were filed Jan. 23, 2004 ;

"Semiconductor-Type Processing for Solid-State Lasers", U.S. Provisional Patent Applications, Ser. No. 60/543,086, was filed Feb. 9, 2004; and "Pulse Streaming of Optically-Pumped Amplifiers", U.S. Provisional Patent Applications, Ser. No. 60/546,065, was filed Feb. 18, 2004. "Pumping of Optically-Pumped Amplifiers" was filed Feb. 26, 2004.

Although the present invention and its advantages have been described in detail, it should be understood that various changes, substitutions and alterations can be made herein without departing from the spirit and scope of the invention as defined by the appended claims. The body, for example, can be of any material, including metal or diamond. Moreover, the scope of the present application is not intended to be limited to the particular embodiments of the process, machine, manufacture, composition of matter, means, methods and steps described in the specification, but only by the claims.

What is claimed is:

1. A method of surgical material removal from a body by optical-ablation with controlled pulse energy from a fiber amplifier, comprising:

inputting an ablation-threshold-pulse-energy-for-material-being-ablated signal;

generating a series of wavelength-swept-with-time pulses using an optical oscillator;

controlling pulse energy based on the ablation-threshold-pulse-energy-for-material-being-ablated signal either by selecting pulses from the oscillator generated series of wavelength-swept-with-time pulses, wherein the fraction of pulses selected can be controllably varied to give a selected pulse repetition rate that is a fraction of the oscillator repetition rate, or by passing electrical current through at least one pump diode to generate pumping light, optically pumping the fiber amplifier with the pumping light, and controlling pump diode current;

amplifying the wavelength-swept-with-time pulse with the fiber-amplifier;

time-compressing the amplified pulse and illuminating a portion of the body with the time-compressed optical pulse, whereby controlling the pulse selection and/or the pump diode current controls the pulse energy; and determining a volumetric removal rate from the pulse energy and the threshold-pulse-energy-for-material-being-ablated signal.

2. The method of claim 1, wherein a volume of material to be ablated is inputted and ablation is performed for a length of time to remove that volume at the volumetric removal rate.

3. The method of claim 1, wherein the ablation-threshold-pulse-energy-for-material-being-ablated signal is inputted by a multi-position selector switch indicating classes of materials, which is set to one of the classes and directly or indirectly selects a volume removal per pulse by an average pulse having an energy in the range of between about 2.5 and about 3.6 times ablation threshold for the selected class.

4. The method of claim 1, wherein the oscillator, amplifier and compressor are within a man-portable system.

5. The method of claim 1, wherein the compression is done in an air-path between gratings compressor.

6. The method of claim 1, wherein the compressed optical pulse has a sub-picosecond duration.

7. The method of claim 1, wherein the oscillator pulse has a duration between about 10 picoseconds and about one nanosecond.

8. The method of claim 1, wherein the ablation is from an outside surface of the body.

9. The method of claim 1, wherein the ablation is done inside of the body.

10. The method of claim 1, wherein more than one amplifiers are used in a mode where amplified pulses from one amplifier are delayed to arrive one or more nanoseconds after those from any other amplifier, to allow control of ablation rate independent of pulse energy.

11. The method of claim 1, wherein the pulse energy applied to the body is between about 2.5 and about 3.6 times ablation threshold of the body portion being ablated.

12. The method of claim 1, wherein a depth of material to be ablated is inputted and ablation is performed for a length of time to remove material to that depth from an area being ablated at the volumetric removal rate.

13. A method of material removal from a body by optical-ablation with controlled pulse energy from an optical amplifier, comprising:

inputting an ablation-threshold-pulse-energy-for-material-being-ablated signal;

generating a series of wavelength-swept-with-time pulses using an optical oscillator;

controlling pulse energy based on the ablation-threshold-pulse-energy-for-material-being-ablated signal to between 2.5 and 3.6 times ablation threshold;

amplifying the wavelength-swept-with-time pulse with the amplifier;

time-compressing the amplified pulse and illuminating a portion of the body with the time-compressed optical pulse, whereby controlling the pulse selection and/or the pump diode current controls the pulse energy; and determining a volumetric removal rate from the pulse energy and the pulse-energy-for-material-being-ablated signal.

14. The method of claim 13, wherein a volume of material to be ablated is inputted and ablation is performed for a length of time to remove that volume at the volumetric removal rate.

15. The method of claim 13, wherein the ablation-threshold-pulse-energy-for-material-being-ablated signal is inputted by a multi-position selector switch indicating classes of materials, which is set to one of the classes and directly or indirectly selects a volume removal per pulse by an average pulse having an energy in the range of about 2.5 and about 3.6 times ablation threshold for the selected class.

16. The method of claim 13, wherein a depth of material to be ablated is inputted and ablation is performed for a length of time to remove material to that depth from an area being ablated at the volumetric removal rate.

* * * * *